United States Patent
Zhu et al.

(10) Patent No.: US 9,970,707 B2
(45) Date of Patent: May 15, 2018

(54) WIND PERMEATION-TYPE DRYER CAPABLE OF SCRAPING MATERIAL

(71) Applicant: HUNAN SUNDY SCIENCE AND TECHNOLOGY CO., LTD., Changsha, Hunan (CN)

(72) Inventors: Xiande Zhu, Changsha (CN); Zhonhtao Zhang, Changsha (CN); Qing Zhu, Changsha (CN)

(73) Assignee: HUNAN SUNDY SCIENCE AND TECHNOLOGY CO., LTD, Changsha, Hunan (CN)

( * ) Notice: Subject to any disclaimer, the term of this patent is extended or adjusted under 35 U.S.C. 154(b) by 0 days. days.

(21) Appl. No.: 15/321,730

(22) PCT Filed: Oct. 28, 2015

(86) PCT No.: PCT/CN2015/093094
§ 371 (c)(1),
(2) Date: Dec. 22, 2016

(87) PCT Pub. No.: WO2016/066105
PCT Pub. Date: May 6, 2016

(65) Prior Publication Data
US 2017/0138667 A1    May 18, 2017

(30) Foreign Application Priority Data
Oct. 31, 2014 (CN) .......................... 2014 1 0599545

(51) Int. Cl.
*F26B 25/04* (2006.01)
*F26B 9/06* (2006.01)
(Continued)

(52) U.S. Cl.
CPC ................ *F26B 25/04* (2013.01); *C10L 5/04* (2013.01); *C10L 9/08* (2013.01); *F26B 3/04* (2013.01);
(Continued)

(58) Field of Classification Search
CPC ....... G01N 33/40; F26B 3/0923; F26B 17/12; F26B 25/04; F26B 25/02; F26B 25/00;
(Continued)

(56) References Cited

U.S. PATENT DOCUMENTS

| 2,092,307 A | * | 9/1937 | Gaffney | .................. B02C 13/14 209/139.1 |
| 5,238,193 A | * | 8/1993 | Pearce | .................... B02C 17/16 241/19 |
| 5,785,578 A | * | 7/1998 | Thoresen | ................ B24B 7/228 451/14 |

FOREIGN PATENT DOCUMENTS

| CN | 2114124 U | 8/1992 |
| CN | 102989204 A | 3/2013 |
| CN | 204227832 U | 3/2015 |

* cited by examiner

*Primary Examiner* — Kenneth Rinehart
*Assistant Examiner* — Raymond Williamson
(74) *Attorney, Agent, or Firm* — Raymond Y. Chan; David and Raymond Patent Firm

(57) ABSTRACT

A wind permeation-type dryer capable of scraping material has a cavity and includes a heating assembly. The experiment cavity and a dropping cavity; the experiment cavity is located above the dropping cavity. The heating assembly communicates with the experiment cavity or the dropping cavity. The cavity is provided with a sieve tray assembly therein for placing materials. The assembly is provided with a rotating scraping assembly provided thereabove for scraping and flattening the materials on the sieve tray assembly. The rotating scraping assembly includes a rotating drive
(Continued)

piece, a scraping sheet, and a rotating rod, wherein one end of the rotating rod is connected to the rotating drive piece and the other end of the rotating rod is connected to the scraping sheet adjacent to the sieve tray assembly. The rotating drive piece drives the rotating rod to rotate so as to drive the scraping sheet to rotate together therewith, such that the materials contacting the scraping sheet is scraped and flattened. The device has an automatic sample flattening function, ensuring the uniformity of sample drying and increasing a working efficiency.

2 Claims, 2 Drawing Sheets

(51) Int. Cl.
  *C10L 9/08* (2006.01)
  *F26B 3/04* (2006.01)
  *G01N 1/44* (2006.01)
  *C10L 5/04* (2006.01)
(52) U.S. Cl.
  CPC ............... *F26B 9/06* (2013.01); *G01N 1/44* (2013.01); *C10L 2290/08* (2013.01); *C10L 2290/60* (2013.01)
(58) Field of Classification Search
  CPC ...... F26B 3/04; F26B 3/14; F26B 3/06; F26B 3/00; F26B 9/00; F26B 9/06; F26B 9/082; F26B 11/12; F26B 11/22; B02C 19/20; B02C 13/14
  USPC ......... 110/104 R, 106, 218, 224, 232; 34/61, 34/384
  See application file for complete search history.

WIND PERMEATION-TYPE DRYER CAPABLE OF SCRAPING MATERIAL

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an apparatus for making coal samples, and more particularly to a wind permeation-type dryer capable of scraping material.

Description of Related Arts

Analysis of characteristics of coal involves a process of sampling analysis of the coal. Coal is a non-homogeneous material, such as its particle size and quality characteristics of distribution. The original coal to be sampled for analysis is relatively large (from tens to tens of thousands of tons). The process of obtaining sample that is able to mostly represent the quality and characteristics of all the coal to be sampled is called "sampling". Presently, there are different methods of sampling such as mechanical sampling, manual sampling, and semi-mechanical sampling. All countries have made compulsory standards respectively that must be followed in sampling.

After samples being sampled following the compulsory standards, the next process is sample preparation, wherein standards of the sample preparation process include gradually reducing the particle size of the samples and gradually decreasing the mass of the samples until they meet the condition required for analysis or testing in the laboratory while under a premise of not destroying the representativeness of the samples. The sample preparation process commonly includes the steps of air-drying, sample reduction, sample division, and sample pulverizing. The process of air-drying is to bring the moisture of the samples near to equilibrium with the atmosphere in the area in which the steps of sample reduction and division to take place so as to facilitate the following steps of sample reduction and sample division. The samples may also be dried by a way of heating, but temperature of the heating should be controlled under 50° C. The process of sample reduction is to reduce the particle size of the samples. The process of sample division is to decrease the mass of the samples while maintaining their representiveness, wherein the remaining samples after the sample division must represent the coal characteristics of the samples before the step of sample division. The step of sample division is the only step in the sample preparation process for decreasing the quantity of the coal samples while the coal samples are not allowed to be lost in quantity in other steps of the sample preparation because any lost of samples in the steps other than sample division (such as coal powder loss, selective loss of waste rock, and etc.) can change the characteristics of the coal samples. Any selective loss of the samples (may not be man-made) is absolutely not allowed during the process of the sample preparation.

With respect to the step of drying the coal samples, there are mainly two methods to reduce a moisture of the coal samples presently:

(1) A method of drying by natural air: This method doesn't change the quality characteristics of the coal. However, the efficiency is too low, the cost time is too much (generally 24-48 hours), and the space occupied is relatively too big.

(2) A method of drying by hot air and a large oven: This method uses a heating lamp with high power or an oven with high power to dry the coal samples and reduce the moisture of the coal samples. Since this method doesn't analyze the two processes of mass transfer during the process of reducing the moisture of the samples, the evaporation only happens on the surface of materials and the moisture in inner layers of the materials can hardly be evaporated out. If the air on the surface of the materials reaches saturation of water absorption, the air on the surface of the materials will no longer absorb into moisture any more. If the air on the surface of the materials is not to be sucked off or exchanged timely, the evaporation will stop essentially. Thus, this method is not efficient as it cannot quickly reduce the moisture of the materials and cost too much time. Since a common fan is applied on the oven, the rate of air exchanging and its efficiency are very low, which lead to the air in the oven approach to the point of water saturation. Thus, the efficiency of using the oven to dry the materials with rich moisture is very poor.

Another method to reduce moisture is based on ventilation, wherein the method uses hot air to blow through the materials to reduce the moisture of the materials. However, conventional equipment always have the following problems:

(1) A low level automation, non-homogeneity drying caused by a disorderly piling of the coal samples, low efficiency of reducing the moisture of the coal samples, and high labor intensity of operators.

(2) Prolonging the process of reducing the moisture of the samples for the coal samples piled on the bottom layer, which may destroy the coal samples piled on the outer layer, so as to decrease the quality and accuracy of the coal samples.

(3) Prolonging the process of reducing the moisture of the samples, which causes a high-energy consumption of the equipment and influences the service life of the equipment.

SUMMARY OF THE PRESENT INVENTION

In view of the problems existing in the prior arts, the present invention features a wind permeation-type dryer capable of scraping material, which has a simple structure, easy operation, high efficiency of reducing moisture of samples, low energy consumption, improves accuracy of sample preparation, and reduces labor intensity of operators.

Another advantage of the present invention is to provide a wind permeation-type dryer capable of scraping material, wherein the wind permeation-type dryer capable of scraping material has a function of automatically scraping and flattening samples, so as to ensure the samples are dried evenly, improve efficiency, lower labor intensity and enhance safety.

Another advantage of the present invention is to provide a wind permeation-type dryer capable of scraping material, wherein the wind permeation-type dryer capable of scraping material not only can achieve up-and-down movement and rotation movement at the same time, but also respectively achieve up-and-down movement and rotation movement.

Another advantage of the present invention is to provide a wind permeation-type dryer capable of scraping material, wherein the wind permeation-type dryer capable of scraping material shortens the process of reducing moisture of samples while lowers energy consumption and prolongs service life of equipment.

Additional advantages and features of the invention will become apparent from the description which follows, and may be realized by means of the instrumentalities and combinations particular point out in the appended claims.

According to the present invention, the foregoing and other objects and advantages are attained by a wind permeation-type dryer capable of scraping material, which comprises:

a cavity comprising an experiment cavity and a dropping cavity, wherein the experiment cavity is provided above the dropping cavity;

a heating assembly communicated with the experiment cavity or the dropping cavity; a sieve tray assembly disposed in the cavity; and a rotating scraping assembly provided above the sieve tray assembly for scraping and flattening materials on the sieve tray assembly, wherein the rotating scraping assembly comprises a rotating drive piece, a scraping sheet, and a rotating rod, wherein one end of the rotating rod is connected to the rotating drive piece and the other end of the rotating rod is connected to the scraping sheet which is adjacent to the sieve tray assembly, wherein when the rotating drive piece drives the rotating rod to rotate so as to drive the scraping sheet to rotate together therewith, the materials contacting the scraping sheet is scraped and flattened.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
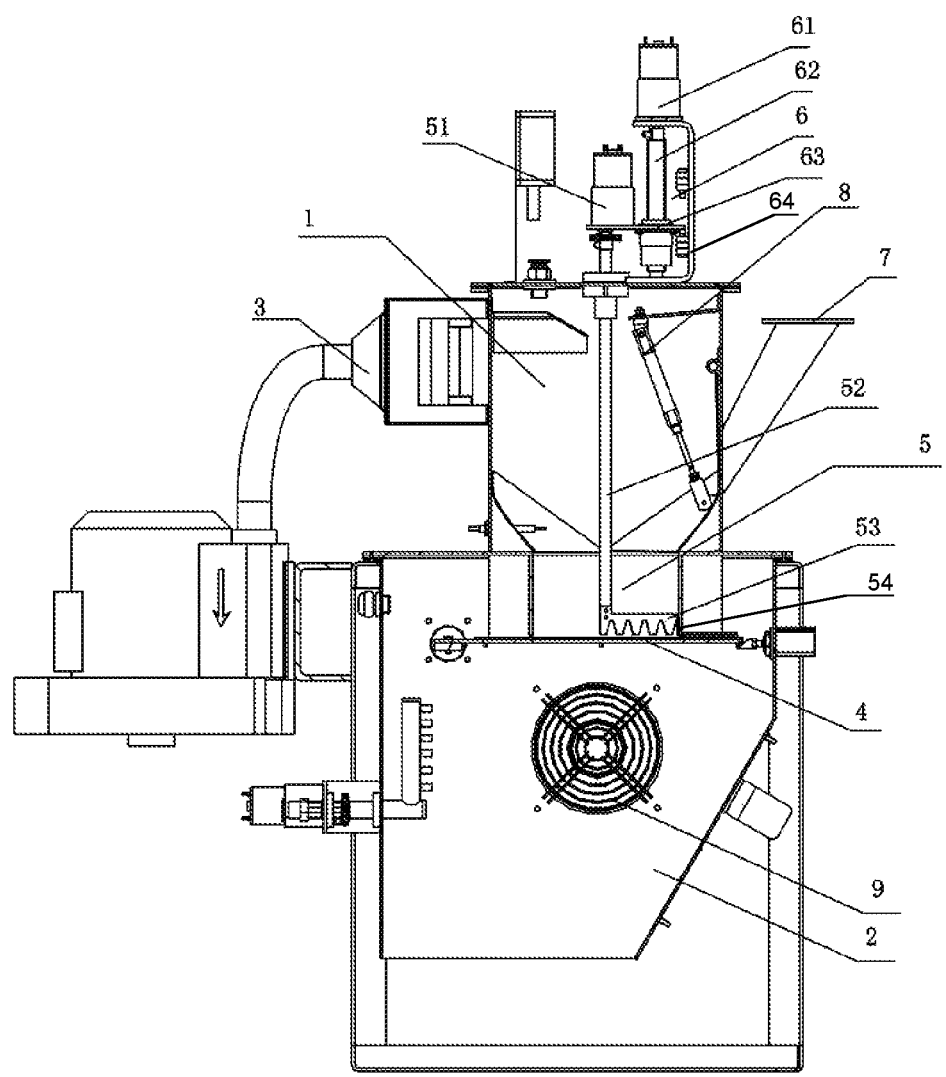
FIG. 1 is a structural schematic view of a wind permeation-type dryer capable of scraping material according to a preferred embodiment of the present invention.
Figure 2:
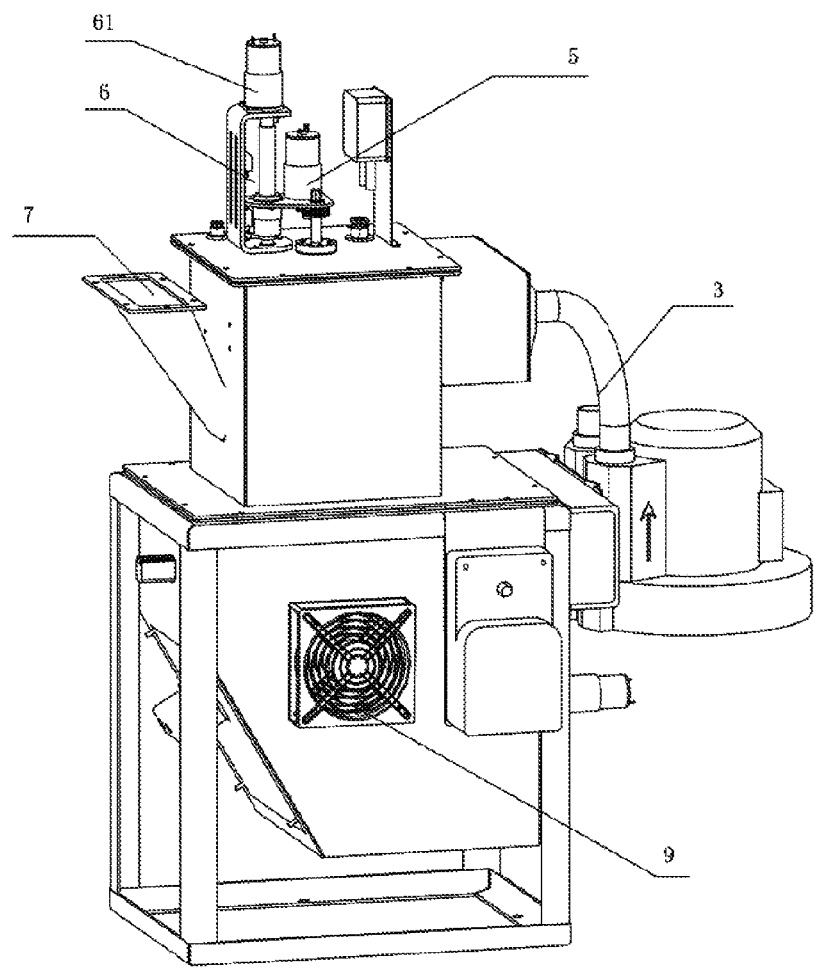
FIG. 2 is a perspective view of a wind permeation-type dryer capable of scraping material according to the above-preferred embodiment of the present invention.
Figure 3:
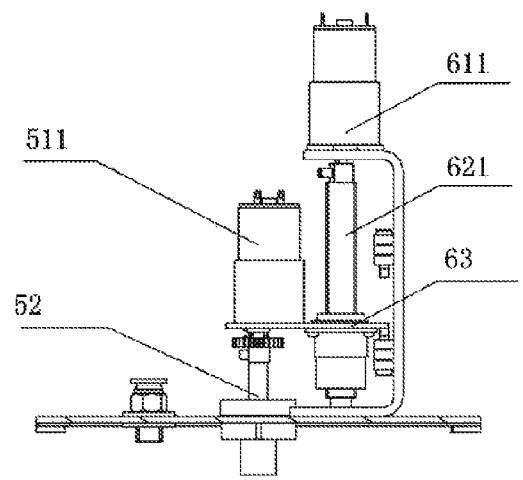
FIG. 3 is a structural schematic view of a rotating scraping assembly and an elevator assembly according to the above-preferred embodiment of the present invention.

As shown in FIG. 1 and FIG. 2, a wind permeation-type dryer capable of scraping material according to a preferred embodiment of the present invention is illustrated, wherein the wind permeation-type dryer capable of scraping material has a cavity which has an experiment cavity 1 and a dropping cavity 2. The cavity 1 is provided above the dropping cavity 2. The wind permeation-type dryer comprises a heating assembly 3 communicated with the experiment cavity 1 or the dropping cavity 2, a sieve tray assembly 4 provided in the cavity for containing materials, and a rotating scraping assembly 5 provided above the sieve tray assembly 4 for scraping and flattening the materials on the sieve tray assembly 4. The scraping assembly 5 comprises a rotating drive piece 51, a rotating rod 52, and a scraping sheet 53, wherein one end of the rotating rod 52 is connected to the rotating drive piece 51 and the other end of the rotating rod 52 is connected to the scraping sheet 53 which is adjacent to the sieve tray assembly 4, wherein when the rotating drive piece 51 drives the rotating rod 52 to rotate so as to drive the scraping sheet 53 to rotate together therewith, the materials contacting the scraping sheet 53 are scraped and flattened.

In order to evenly flatten the materials when the materials are disorderly piled on the sieve tray assembly 4, the rotating drive piece 51 drives the rotating rod 52 to rotate, and at the same time drives the scraping sheet 53 to rotate together so as to scrap and flatten the materials through the scraping sheet 53. When hot air blows through the materials, the materials are guarantee to be dried evenly having been scraped and flattened, so as to improve working efficiency. According to the present embodiment, the rotating drive piece 51 is a rotating motor 511, wherein one end of the rotating rod 52 is connected to the rotating motor 511 and the other end of the rotating rod 52 is connected to the scraping sheet 53.

According to another embodiment of the present invention, the wind permeation-type dryer capable of scraping material further comprises an elevator assembly 6 for an up and-down movement, wherein the elevator assembly 6 comprises an elevator drive assembly 61, an elevator transmission assembly 62, and a connecting sheet 63, wherein the elevator drive assembly 61 is connected to one end of the connecting sheet 63 through the elevator transmission assembly 62 so as to move up and down, and the other end of the connecting sheet 63 is connected to the rotating scraping assembly 5.

According to another embodiment of the present invention, the elevator assembly 6 of the wind permeation-type dryer capable of scraping material is mounted on a top panel of the experiment cavity 1 through a rack 64, wherein the elevator drive assembly 61 comprises an elevator motor 611. The elevator transmission assembly 62 comprises a screw assembly 621, wherein the screw assembly 621 is matched with the elevator motor 611 to drive the rotating scraping assembly 5 to move up and down through the connecting sheet 63.

The process of reducing the moisture of the samples is a process of mass transfer. A flowing air gradually takes the moisture of the samples away. The process of reducing the moisture comprises of two stages. A first stage is changing the moisture on the surface of the materials from a liquid phase to a vapor phase; a second stage is evaporating the water steam from the surface of the materials, and the flowing air taking away the permeated air on the surface of the material. The two stages are related to the surrounding temperature of the materials, wherein the evaporation on the surface of the materials and the quantity of the moisture which the surrounding air can absorb into are presented a function with the temperature, such that as the temperature increases, the evaporated rate is faster and the quantity of air can absorb larger quantity of moisture. However, the temperature can influence the physical and chemical properties of the coal samples if it reaches a certain level. The international standards regulate that the temperature cannot be above 40° C. The national standards regulate that the temperature cannot be above 50° C. The present invention adopts a method that reduces the moisture by blowing air through the coal samples, effectively expands the evaporation area of the materials and improves the efficiency several to a dozen times.

Meanwhile, in order to improve the efficiency, the wind permeation-type dryer capable of scraping material further comprises a rotating scraping assembly 5 provided above the sieve tray assembly 4 for flattening and scraping the materials on the sieve tray assembly 4, wherein the materials are rotated and flattened so as to guarantee the materials are dried evenly, that improves the efficiency and reduces the labor intensity of operators. The wind permeation-type dryer capable of scraping material further through the disposition of the elevator assembly 6, which drives the movement of the rotating scraping assembly 5, not only can achieve up and-down movement and rotation movement at the same time, but also respectively achieve up and-down movement and rotation movement, so that the materials are scraped and flattened more evenly. Thus, the level of the automation is improved, the process of reducing the moisture of the materials is shortened, the accuracy and the integrity of the materials are enhanced, the energy consumption of the equipment is lowered, and the service time of the equipment is prolonged.

According to another embodiment of the present invention, an end of the scraping sheet 53, which is adjacent to the sieve tray assembly 4, has a line shape. In any one of other embodiments, an end of the scraping sheet 53 can have a slant line shape or a dentate shape.

According to another embodiment of the present invention, a silicon sheet 54 is provided on the scraping sheet 53, which is adjacent to a side wall of the experiment cavity 1, so as to enlarge the scraping area, wherein the silicon is deformed to avoid a scratch between the scraping sheet 53 and a bottom cavity in the event that the bottom cavity is not round enough.

According to another embodiment of the present invention, a side wall of the experiment cavity 1 has a feeding opening 7 provided thereon, wherein a valve assembly 8 is provided on the feeding opening 7.

According to another embodiment of the present invention, the dropping cavity 2 comprises a fan 9 disposed thereon for exhausting the air out of the dropping cavity 2 timely for ventilation to avoid forming a condensation on an inner surface of the dropping cavity 2.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A wind permeation-type dryer capable of scraping material, having a cavity which has a dropping cavity and an experiment cavity provided above said dropping cavity, and comprising:
   a heating assembly communicated with at least one of said experiment cavity and said dropping cavity,
   a sieve tray assembly disposed in said cavity,
   a rotating scraping assembly provided above said sieve tray assembly for scraping and flattening materials on said sieve tray assembly, wherein said rotating scraping assembly comprises a rotating drive piece, a scraping sheet, and a rotating rod, wherein one end of said rotating rod is connected to said rotating drive piece and another end of said rotating rod is connected to said scraping sheet which is adjacent to said sieve tray assembly, wherein when said rotating drive piece drives said rotating rod to rotate so as to drive said scraping sheet to rotate together therewith, said materials contacting said scraping sheet are flattened and scraped, wherein said rotating drive piece is a rotating motor, wherein said end of said rotating rod is connected to said rotating motor and said other end of said rotating rod is connected to said scraping sheet; and
   an elevator assembly for driving said rotating scraping assembly to move up and down, wherein said elevator assembly comprises an elevator drive assembly, an elevator transmission assembly and a connecting sheet, wherein said elevator drive assembly is connected to one end of said connecting sheet through said elevator transmission assembly to move up and down, and another end of said connecting sheet is connected to said rotating scraping assembly to enable both rotating movement and up and down movement of said scraping sheet, wherein said elevator assembly is mounted on a top panel of said experiment cavity through a rack, wherein said elevator drive assembly comprises an elevator motor, wherein said elevator transmission assembly comprises a screw assembly, wherein said screw assembly is matched with said elevator motor to drive said rotating scraping assembly to move up and down through said connecting sheet, wherein a silicon sheet is provided on an end of said scraping sheet which is adjacent to a side wall of said experiment cavity.

2. A wind permeation-type dryer capable of scraping material, having a cavity which has a dropping cavity and an experiment cavity provided above said dropping cavity, and comprising:
   a heating assembly communicated with at least one of said experiment cavity and said dropping cavity,
   a sieve tray assembly disposed in said cavity,
   a rotating scraping assembly provided above said sieve tray assembly for scraping and flattening materials on said sieve tray assembly, wherein said rotating scraping assembly comprises a rotating drive piece, a scraping sheet, and a rotating rod, wherein one end of said rotating rod is connected to said rotating drive piece and another end of said rotating rod is connected to said scraping sheet which is adjacent to said sieve tray assembly, wherein when said rotating drive piece drives said rotating rod to rotate so as to drive said scraping sheet to rotate together therewith, said materials contacting said scraping sheet are flattened and scraped, and
   an elevator assembly for driving said rotating scraping assembly to move up and down, wherein said elevator assembly comprises an elevator drive assembly, an elevator transmission assembly and a connecting sheet, wherein said elevator drive assembly is connected to one end of said connecting sheet through said elevator transmission assembly to move up and down, and another end of said connecting sheet is connected to said rotating scraping assembly to enable both rotating movement and up and down movement of said scraping sheet, wherein said elevator assembly is mounted on a top panel of said experiment cavity through a rack, wherein said elevator drive assembly comprises an elevator motor, wherein said elevator transmission assembly comprises a screw assembly, wherein said screw assembly is matched with said elevator motor to drive said rotating scraping assembly to move up and down through said connecting sheet, wherein a silicon sheet is provided on an end of said scraping sheet which is adjacent to a side wall of said experiment cavity.

* * * * *

UNITED STATES PATENT AND TRADEMARK OFFICE
CERTIFICATE OF CORRECTION

PATENT NO. : 9,970,707 B2  
APPLICATION NO. : 15/321730  
DATED : May 15, 2018  
INVENTOR(S) : Xiande Zhu, Zhongtao Zhang and Qing Zhu Page 1 of 1

It is certified that error appears in the above-identified patent and that said Letters Patent is hereby corrected as shown below:

On the Title Page

Item [72] Name of Second Inventor: "Zhonhtao Zhang" should read -Zhongtao Zhang-.

Signed and Sealed this
Eighteenth Day of September, 2018

Andrei Iancu
*Director of the United States Patent and Trademark Office*